(12) United States Patent
Mueller et al.

(10) Patent No.: US 6,896,695 B2
(45) Date of Patent: May 24, 2005

(54) STENT

(75) Inventors: Heinz Mueller, Erlangen (DE); Claus Harder, Uttenreuth (DE)

(73) Assignee: Biotronik Mess-Und Therapiegeraete GmbH & Co., Berlin (DE)

( * ) Notice: Subject to any disclaimer, the term of this patent is extended or adjusted under 35 U.S.C. 154(b) by 0 days.

(21) Appl. No.: 09/804,975

(22) Filed: Mar. 13, 2001

(65) Prior Publication Data

US 2002/0022877 A1 Feb. 21, 2002

(30) Foreign Application Priority Data

Mar. 15, 2000 (DE) ......................................... 100 12 460

(51) Int. Cl.[7] .............................................. A61F 2/06
(52) U.S. Cl. .................................................. 623/1.15
(58) Field of Search ............................. 623/1.15, 1.12; 606/194

(56) References Cited

U.S. PATENT DOCUMENTS

| 4,655,771 | A |   | 4/1987  | Wallsten              |
|-----------|---|---|---------|-----------------------|
| 5,104,404 | A |   | 4/1992  | Wolff                 |
| 5,879,381 | A | * | 3/1999  | Moriuchi et al. ...... 623/1.15 |
| 5,935,162 | A | * | 8/1999  | Dang .................. 623/1.15 |
| 5,968,093 | A | * | 10/1999 | Kranz .................. 623/1.15 |
| 6,375,677 | B1| * | 4/2002  | Penn et al. ........... 623/1.16 |

FOREIGN PATENT DOCUMENTS

| DE | 196 53 708 C2 | 4/1998 |
| DE | 196 53 721 A1 | 4/1998 |
| DE | 196 53 709 A1 | 7/1998 |
| DE | 197 49 691 A1 | 4/1999 |
| WO | WO 98/07386 | 2/1998 |
| WO | WO 99/18888 | 4/1999 |

OTHER PUBLICATIONS

Serruys, "Handbook of Coronary Stents," Rotterdam Thoraxcenter Group.

* cited by examiner

Primary Examiner—Alvin Stewart
(74) Attorney, Agent, or Firm—Hahn Loeser + Parks, LLP; John J. Cunniff

(57) ABSTRACT

A stent, in particular a coronary stent, comprising at least two tubular portions which are arranged adjacently in the longitudinal direction of the stent and which comprise a plurality of interconnected, substantially cell-shaped elements which have an orientation and are connected together in the longitudinal direction of the stent by way of at least one first connecting means, wherein the elements are of such an arrangement and/or configuration that the ends of the elements which are in the longitudinal direction of the stent define an edge contour extending around the stent in a wave-like configuration in the peripheral direction thereof, and wherein the mutually adjoining edge contours of two tubular portions extend around the stent substantially in in-phase relationship.

41 Claims, 10 Drawing Sheets

STENT

The invention concerns a stent, in particular a coronary stent, comprising at least two tubular portions which are arranged adjacently in the longitudinal direction of the stent and which comprise a plurality of interconnected, substantially cell-shaped elements which have an orientation and are connected together in the longitudinal direction of the stent by way of at least one first connecting means, wherein the elements are of such an arrangement and/or configuration that the ends of the elements which are in the longitudinal direction of the stent define an edge contour extending around the stent in a wave-like configuration in the peripheral direction thereof.

BACKGROUND OF THE ART

Stents are known from the state of the art in many different forms. They are used inter alia in connection with percutaneous transluminal angioplasty (PTCA= percutaneous transluminal coronary angioplasty) in vascular surgery. Stents however can also serve to dilate other openings in the body or to hold them in a diluted state. Those medical procedures firstly presuppose that the location of the constriction in the respective vessel has been determined. Then for example in PTCA a so-called angioplasty balloon is pushed into the artery which has the constriction, the so-called stenosis, and moved to the location of the stenosis. The balloon is then expanded so that the radially outwardly directed force of the balloon dilates the stenosis and in the optimum situation restores the original passage cross-section of the previously constricted artery.

The stents set forth in the opening part of this specification were developed to maintain the dilated condition of the artery subsequently to the dilation operation. The stents thus serve to prevent the recurrence of a stenosis. The success of so-called stenting however depends inter alia on how uniformly the stent can bear against the inside of the vessel wall. For, the more uniformly the vessel wall can be supported by the stent, the more probable it is that vessel constrictions cannot occur again in the region of the installed stent. Accordingly, a uniform and regular stent structure produces a relatively smooth inside surface in the vessel, to which blood particles can stick only with difficulty. In addition, proliferation of the intima into the interior of the vessel through the stent is also prevented to a greater degree by a uniform and regular stent structure.

Stents having the above-mentioned closed structure are known from the state of the art. U.S. Pat. No. 4,655,771 for example discloses a stent, a so-called wall stent, having a closed structure which is formed from two wires which are woven in a uniform mesh-like configuration and which extend helically on the longitudinal axis of the stent.

The advantage of the closed structure in terms of covering the inside wall of the vessel is however at the cost of the disadvantage that those stents involve relative longitudinal stiffness during insertion of the stent in particular into narrow blood vessels. Those stents therefore do not make it possible in the optimum fashion for the stent to be introduced through possibly very sharply curved vessel portions of the coronary blood vessels, upon being introduced in a direction towards the stenosis to be treated. Closed structures also give rise to problems in regard to using them in the region of curved vessel portions, by virtue of their longitudinal stiffness. A particular disadvantage with a closed structure like the wall stent moreover is that substantial longitudinal contraction occurs upon dilation.

In order to avoid the disadvantages with stents having a closed structure, stents have been developed which are of a so-called modular structure. In those modular-structure stents, individual portions which are provided with a closed structure are connected together by flexible connections. Stents of that kind are known for example from U.S. Pat. No. 5,104,404.

A stent of the general kind set forth is also known by the name Tenax® (Handbook of Coronary Stents, Martin Dunitz, Ltd, London, 1998, pages 121 ff). In that stent the adjacent edge regions of adjacent tubular portions extend in displaced relationship with each other through half a period in the peripheral direction of the stent for reasons of compensation in respect of length. That provides for compensation for the reduction in length of the stent, which results upon expansion from the reduction in length of the cell-shaped elements in the longitudinal direction of the stent.

A disadvantage with the known modular or segmented stents however is that often in the expanded condition they have relatively large gaps in the covered region of the wall of the vessel, while it is precisely segmented stents that also have such gaps of different sizes. Because the inside wall of the vessel is covered by the webs or bars of the stent in a more or less irregular fashion in the expanded condition of the stent, and in particular also due to the relatively large areas that remain free between the bars or webs of the stent, the tissue of the inside wall of the vessel, after implantation of the stent into the vessel, can suffer from prolapse, which can lead to renewed constriction of the vessel, a so-called re-stenosis.

SUMMARY OF THE INVENTION

Therefore the object of the present invention is further to develop a stent of the kind set forth in the opening part of this specification, in such a way that the above-mentioned disadvantages are avoided and a covering for the inside wall of the vessel is achieved, whose areas that remain free are reduced in size in comparison with the state of the art.

Based on a stent as set forth in the classifying portion of claim 1, that object is attained by the features recited in the characterising portion of the claim.

The present invention is based on the technical teaching that particularly good coverage for the inside wall of the vessel in question is achieved if the elements are arranged in such a way and additionally or alternatively are of such a configuration that the mutually adjoining edge contours of two tubular portions extend around the stent substantially in in-phase relationship. The fact that the edge contours extend around the stent in phase means that it is possible for the two mutually adjoining tubular portions to be arranged so closely to each other that on the one hand smaller gaps already occur in the stent structure in the non-expanded condition but in particular in the expanded condition of the stent. On the other hand, in that respect more uniform gaps are further advantageously formed in the stent structure. In other words, the invention affords coverage of the inside wall of the vessel, which is more uniform in comparison with the state of the art, over the entire peripheral surface of the expanded stent, and that has an advantageous effect on the re-stenosis rate.

The advantages according to the invention are particularly significant when the stent is expanded in a curved vessel as, in such a situation, the portions at the outside of the curvature of the stent which is expanded in the curved vessel tend to gape open. The influence of that gaping is advantageously suppressed by the configuration according to the invention.

It has been found that the configuration according to the invention, by virtue of a suitable arrangement of the first connecting means and a suitable configuration of the connections between the elements of a tubular portion, makes it possible to achieve adequate compensation for the reduction in length upon expansion.

The distance between the tubular portions in the longitudinal direction of the stent can be selected according to the respective degree of flexibility required or according to the respective attainable minimum radii of curvature of the stent, which are required for the purpose of use involved. The smaller that spacing, the more the elements of adjacent tubular portions come into contact with each other upon curvature of the stent, whereby then further curvature is prevented or is possible only by virtue of the elements being pushed one over the other.

In preferred variants of the stent according to the invention the elements are arranged in such a way and additionally or alternatively are of such a configuration that the edge contours of the two adjacent tubular portions engage into each other in the manner of a tooth configuration. That provides for particularly good, that is to say uniform coverage of the inside wall of the vessel with small gaps of relatively uniform size.

In this respect the expression 'in the manner of a tooth configuration' is to be interpreted as meaning that the elements of adjacent tubular portions in that case do not necessarily touch. On the contrary, in this embodiment, in other words, the individual elements of the one tubular portion preferably come so close to the elements of the adjacent tubular portion that the adjacent elements partially overlap or almost overlap in the longitudinal direction of the stent. Such overlap or partial overlap of adjacent elements of adjacent portions is advantageous in particular when upon dilation of the stent displacement of the individual elements occurs in the longitudinal direction.

The two edge contours of a tubular portion in preferred variants of the stent according to the invention extend relative to each other substantially in in-phase relationship. In other advantageous variants they extend in mutually displaced relationship substantially through half a period. In this respect it will be appreciated that tubular portions of these two variants may possibly be combined together within the stent.

The configuration in accordance with the invention of the edge contours of the tubular portions can be embodied in various ways. Thus, in the respective tubular portion, for example elements of dimensions which are substantially the same in the longitudinal direction of the stent may be arranged in mutually displaced relationship alternately in the longitudinal direction of the stent so that this affords an arrangement of those elements, which is wave-shaped in the peripheral direction of the stent. In other words, in these variants, the length of the elements of the tubular portions in the longitudinal direction of the stent is smaller than the maximum width, as measured in the longitudinal direction of the stent, of the corresponding tubular portion. That then provides a tubular portion, whose edge contours extend in phase with each other.

Edge contours which extend in mutually displaced relationship substantially through half a period can be achieved for example by arranging alternately in the peripheral direction of the stent elements which are of different dimensions in the longitudinal direction of the stent. In this case, the amplitudes of the edge contours can be easily adjusted by suitably selecting the position of the individual elements relative to each other, with respect to the longitudinal direction. Equal amplitudes can be set for example by the center points of the individual elements being aligned with each other in the peripheral direction of the stent.

In preferred variants of the stent according to the invention the respective first connecting means connects elements of the same orientation together. This is advantageous in particular when the individual elements are not of a symmetrical configuration but are of a geometry which is asymmetrical in the longitudinal direction of the stent. The advantage in this respect lies in the extent, which is in principle less, of the reduction in length of the stent as is caused by expansion thereof. That effect is due to the fact that the first connecting means respectively connect together different ends of the asymmetrical elements having an orientation while in the state of the art, in the case of asymmetrical elements having an orientation, it is always the same ends of those elements which are connected together.

That advantage is significant in particular in the case of elements which are of a keyhole shape as in that case, with the present invention, the small arcs of the keyhole-shaped element are connected to the large arcs of the adjacent keyhole-shaped element. In such a case, upon expansion, the small arcs experience greater displacement along the longitudinal axis of the stent than the larger arcs. While the state of the art provides that in each case the small arcs are connected together and accordingly experience a relatively great displacement in the longitudinal direction of the stent, thus resulting in a considerable reduction in the length of the stent, that effect is reduced with the configuration according to the invention. Thus, the structure according to the invention affords a lesser reduction in length of the stent, due to expansion. In that way the reduction in length of the stent which is caused by expansion thereof can be reduced to a minimum.

Simultaneous preferred alternate orientation of the individual elements of each portion in a configuration of being displaced through 180° provides the above-mentioned wave-like arrangement of the individual elements of each tubular portion as viewed in the peripheral direction. In this embodiment, as mentioned, the individual elements of the portion can come so close to the elements of the adjacent portion that the adjacent elements partially overlap or almost overlap in the longitudinal direction of the stent. Such overlap or partial overlap of adjacent elements of adjacent portions is advantageous in particular when the stent involves displacement of the individual elements upon dilation of the stent in the longitudinal direction.

The first connecting means can be of any desired configuration. Preferably the first connecting means, like also the elements themselves, is of a web-like or bar-like configuration. It may also involve any desired arrangement with respect to the longitudinal direction of the stent. Preferably the first connecting means extends substantially parallel to the longitudinal axis of the stent.

Variants of the stent according to the invention, which are preferred because they are extremely flexible, are distinguished in that as few as possible and at most two and preferably only one first connecting means are or is provided for the connection of adjacent tubular portions. In this embodiment which is preferably used with tubular portions with eight elements, the stent is advantageously kept flexible by virtue of the low number of connecting means.

In advantageous embodiments of the stent according to the invention the first connecting means are in mutual alignment over the length of the stent from one portion to another. That affords particularly uniform coverage of the inside surface of the vessel. In that arrangement it is further preferable for each tubular portion to be of an identical configuration so that the uniformity of the stent according to the invention is further increased.

If however optimum flexibility is wanted for the stent, then the first connecting means in an alternative embodiment are arranged in mutually displaced relationship. In this case preferably there are more than two tubular portions and the first connecting means are arranged displaced in the peripheral direction of the stent over the length of the stent from one portion to another. A configuration which is particularly desirable in respect of flexibility of the stent is afforded if in that case the first connecting means are arranged displaced through at least half a period of the edge contour.

In a further preferred embodiment of the invention there are provided second connecting means which connect together the elements of each portion in the peripheral direction of the stents. Those second connecting means are further preferably such that with their longitudinal axis they form an angle relative to the peripheral direction of the respective portion. In this case the connecting means can at the same time also be of an S-shaped configuration. In particular the measure involving the angled arrangement of the connecting means provides for longitudinal displacement of the individual elements along the longitudinal axis of the stent upon dilation thereof.

Thus, further preferred variants of the stent according to the invention are distinguished in that the elements of at least one tubular portion are connected in the peripheral direction of the stent by way of second connecting means which are arranged inclinedly with respect to the peripheral direction and which preferably extend in an S-shape, wherein second connecting means which face in the same peripheral direction of elements in mutually adjoining relationship in the longitudinal direction of the stent are arranged inclinedly in the opposite manner with respect to the peripheral direction. With that design configuration, it is easily possible to add on the longitudinal displacement of the individual elements, which occurs upon expansion and which results from the orientation of the second connecting means in the peripheral direction, by virtue of a suitable displaced arrangement of the first connecting means, over the entire stent, and thus to achieve particularly good compensation for a reduction in length. In that way the reduction in length of the stent which is caused by stent expansion is reduced to a minimum.

The advantages of the structure according to the invention are in particular that only relatively small free areas through which the tissue of the vessel wall could suffer prolapse into the vessel are afforded on the peripheral surface of the stent in the expanded condition between adjacent tubular portions. In preferred variants, those relatively small free areas are afforded by virtue of the fact that elements of identical orientation are connected together. If those elements for example are cells formed from webs or bars in a keyhole shape, then the invention provides that the wider end of the element is connected to the narrower end of the cell-shaped element, which results in the advantageous reduction in size in accordance with the invention of the area which remains free in the expanded condition of the stent.

It is particularly advantageous in the case of the present invention that not only is the size of the free areas reduced, but in particular the size of free areas of a specific shape is reduced. These involve such areas within the peripheral surface of the stent according to the invention, whose closed boundary, in one revolution, has curvatures only in one direction. In particular such areas can be considerably reduced in size in comparison with the state of the art, by virtue of the invention. It is precisely such areas that have been found in the state of the art to be locations at which the tissue can more easily prolapse into the interior of the vessel.

Furthermore, the simple but effective measures of the invention make it possible to achieve the advantages, which are known from the state of the art, of segmented stents, for example the present applicants' stent 'Tenax®'. In particular the good mechanical properties (recoil, collapse pressure, longitudinal flexibility and low crimp profile) are still retained as it is precisely in comparison with the known 'Tenax®' stent that the structure of the tubular portions themselves and the basic manner of connecting adjacent portions do not change.

The present invention further concerns a dilation catheter having a stent according to the invention.

BRIEF DESCRIPTION OF THE DRAWINGS

Further advantageous embodiments of the invention are set forth in the appendant claims or with reference to the description hereinafter of preferred embodiments relating to the accompanying drawings in which:

DETAILED DESCRIPTION OF THE INVENTION

Figure 1:
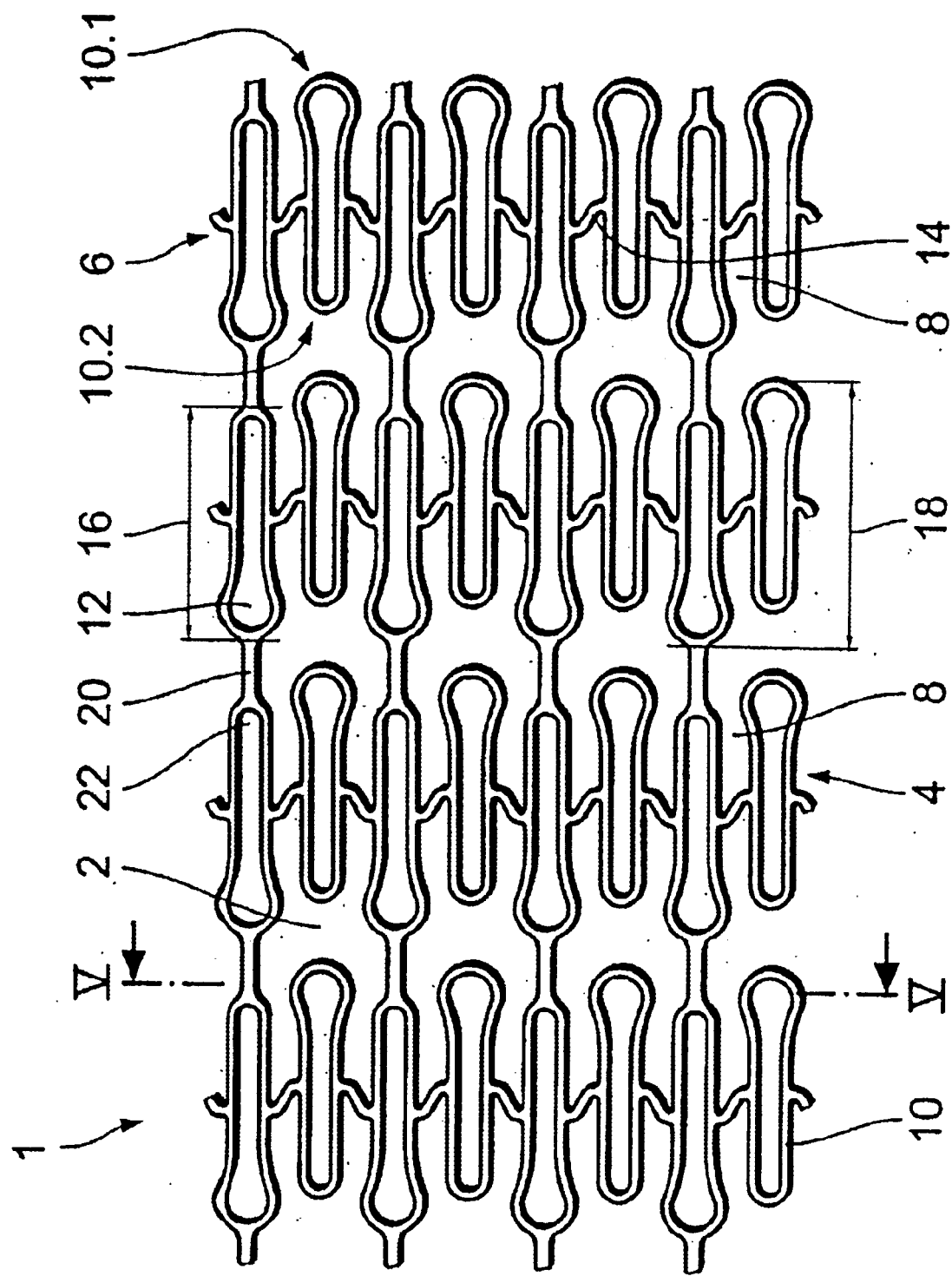
FIG. 1 shows a developed view of a part of the peripheral surface of a stent according to the invention, FIG. 2 diagrammatically shows the development from FIG. 1 in a non-expanded condition (faint lines) and an expanded condition (bold lines)

FIG. 1 shows a stent 1 according to the invention. The stent 1 is shown in FIG. 1 in a form of a part of the development of its peripheral surface 2. In the condition of the stent 1 in which it is ready for operation, the peripheral surface 2 is connected with its side 4 which is shown at the bottom in FIG. 1 to the side 6 which is shown at the top in FIG. 1, thus affording the tubular stent 1 in the configuration in which it is ready for operation.

The peripheral surface 2 is composed of four tubular portions 8 which are also shown as a development in FIG. 1. In FIG. 1, each tubular portion 8 has eight cell-shaped elements 10 which are asymmetrical in the form of a keyhole and which have an orientation. In each tubular portion 8 the cell-shaped elements 10 are respectively arranged adjacent to each other in the peripheral direction of the stent, oriented with their longitudinal axes parallel to the longitudinal axis of the stent 1. Each element 10 involves an identical basic shape. The elements 10 however are arranged in such a way that the keyhole-like basic shape of the elements 10 respectively involves an opposite orientation in adjacent elements 10, that is to say the outwardly bulging ends 12 of the elements 10 are respectively turned through 180° relative to each other, in adjacent elements 10.

The elements 10 which are adjacent in the peripheral direction of the stent are connected together in the peripheral direction of the stent 1 by way of S-shaped second connecting webs or bars 14 serving as second connecting means, and aligned coaxially in the longitudinal direction of the stent. The S-shaped second connecting bars 14 provide that adjacent elements 10 are each displaced a little relative to each other in the longitudinal direction of the stent 1. The length 16 of the elements 10 of each tubular portion 8 is therefore respectively less than the width 18 of each tubular portion 8. Accordingly therefore the ends 10.1 and 10.2 respectively of the elements 10, which are disposed in the longitudinal direction of the stent 1, define for each tubular portion 8 two edge contours which extend around the stent 1 in the peripheral direction thereof in a wave-like configuration in in-phase relationship with each other. In this case the tubular portions 8 are also arranged in such a way that the mutually adjoining edge contours of adjacent tubular portions 8 extend around the stent in in-phase relationship.

The tubular portions 8 are connected together by way of first connecting webs or bars 20 serving as first connecting means. The first connecting bars 20 extend substantially parallel to the longitudinal axis of the stent 1. It will be appreciated however that, in other variants of the invention, the first connecting bars can also be of a different configuration and/or arrangement. In particular, the first connecting bars may also in known fashion involve a configuration which contributes to enhancing the flexibility of the stent. Thus, the first connecting bar in question may for example also extend in an S-shape.

The first connecting bars 20 connect respectively adjacent elements 10 of the portions 8 together, insofar as they connect the outwardly bulging end 12 of an element 10 to the narrow end 22 of an element 10. As shown in FIG. 1, each second element 10 of a tubular portion 8 is connected to the element 10, which is respectively adjacent in the longitudinal direction of the stent 1, of the adjacent tubular portion 8. All elements 10 which are connected by way of a first connecting bar 20 to an adjacent element 10 are also always connected on the respective other side to a further element 10 of the portion 8 which is adjacent on that side, so that all first connecting bars 20 are aligned with each other as viewed in the longitudinal direction. That excludes the elements 10 which are not shown in FIG. 1 and which are arranged at the ends of the stent and which do not have any further first connecting bars 20 towards the edge.

Figure 2:
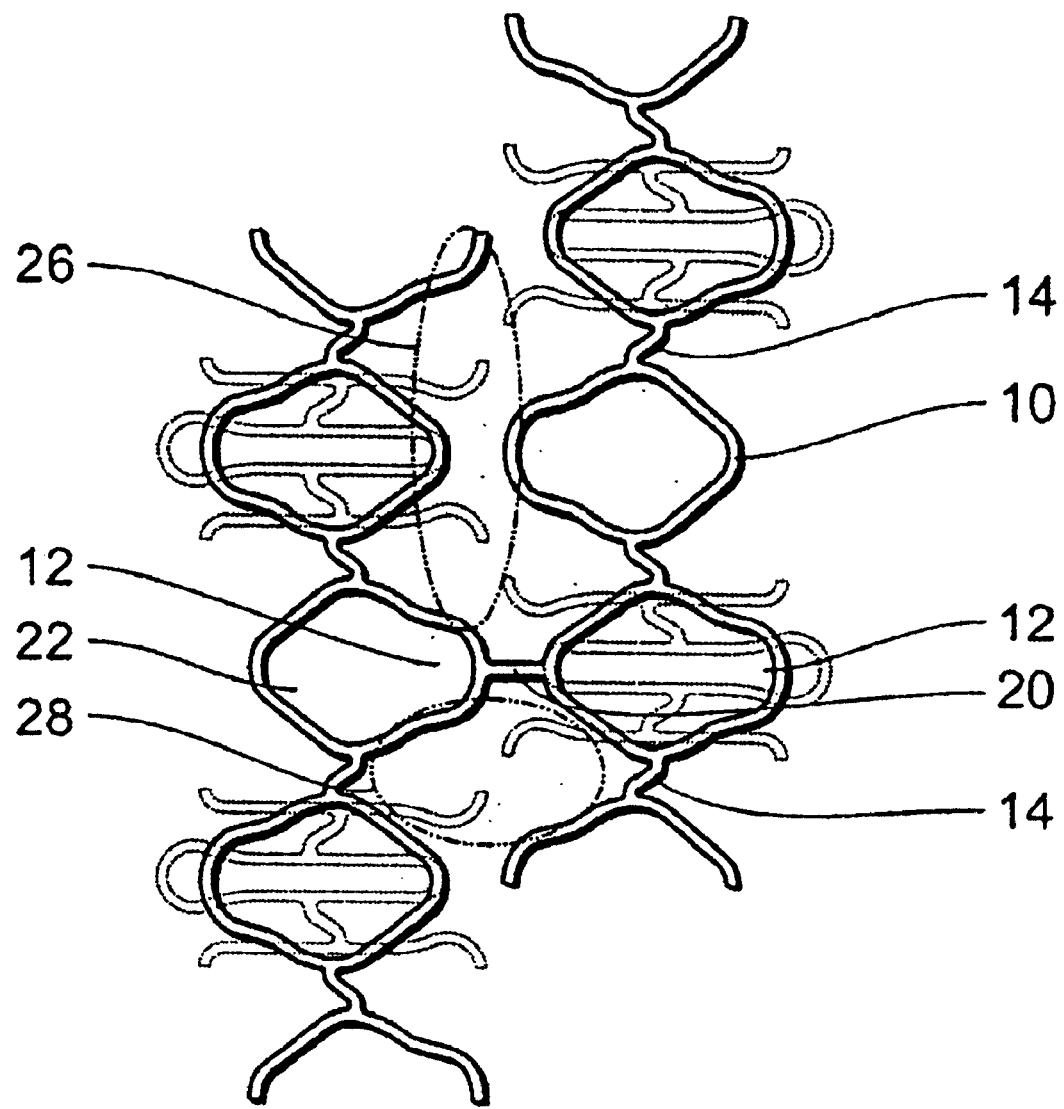
Figure 3:
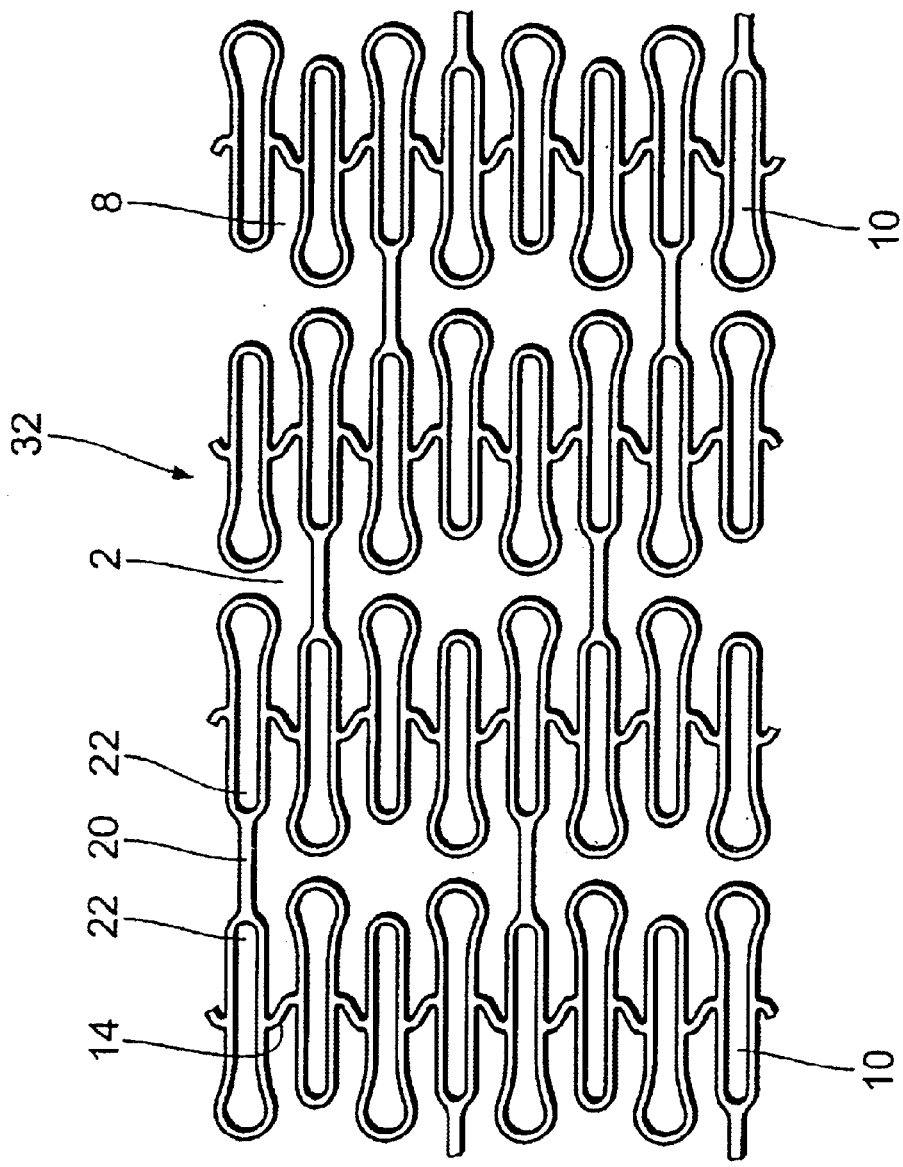
FIG. 3 shows a stent from the state of the art on the basis of the development of its peripheral surface.
Figure 4:
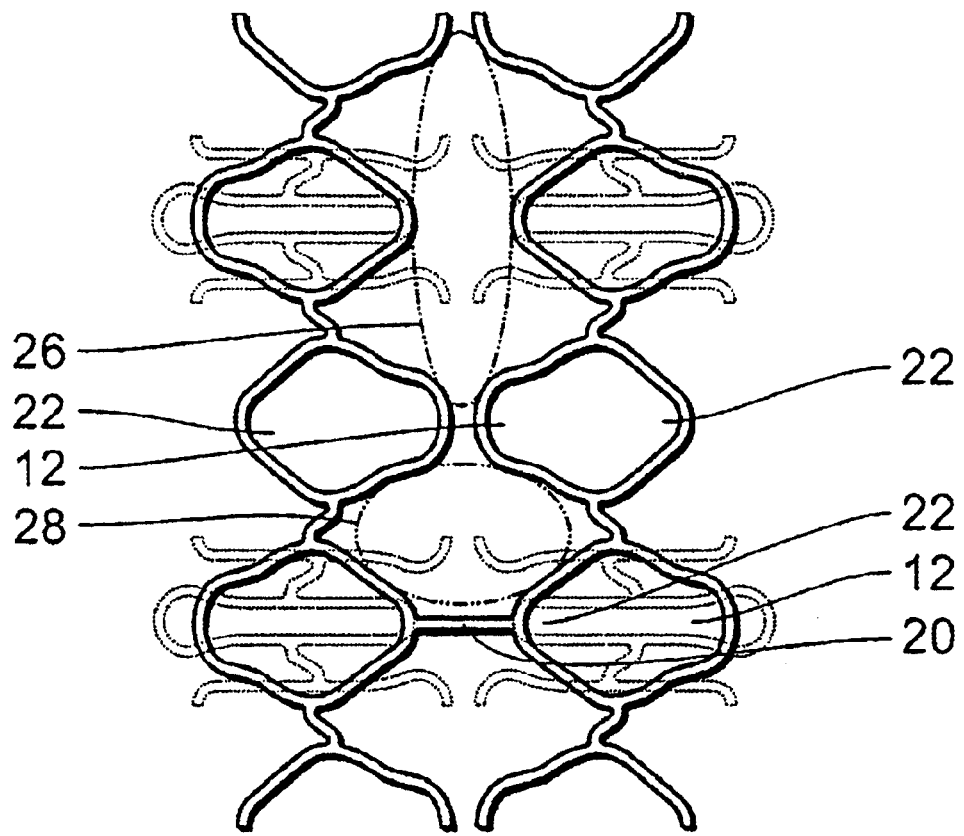
FIG. 4 is a diagrammatic view of the stent of FIG. 3 in the non-expanded condition (dotted lines) and the expanded condition (bold lines)

FIG. 2 is a diagrammatic view of the stent 1 of FIG. 1 in a non-expanded condition (dotted lines) and an expanded condition (bold lines). Parts which correspond to parts in FIG. 1 are denoted in FIG. 2 by the same references. In addition, also shown in FIG. 2 are elliptical areas 26 and 28 which correspond to the free areas 26 and 28 of an expanded stent 32 from the state of the art, as shown in FIGS. 3 and 4. FIG. 2 clearly shows that the free areas 26 and 28 present in FIG. 4 in the expanded condition of a stent 1 according to the invention are no longer present in the same size, thus affording an improvement in the coverage of the inside of a vessel.

FIG. 3 shows a stent from the state of the art. In this case also—in order to make it easier to compare the invention to the state of the art—parts which in substance correspond to those of the stent 1 in FIG. 1 are denoted by the same references. It will be seen from FIG. 3 that, in the state of the art, respective elements 10 of opposite orientation were connected by way of the connecting means 20. In that way, a connection was made between the narrow ends 22 of the respective elements 10 by means of the respective connecting bar 20. In the state of the art that again resulted in the free areas 26 and 28 shown in FIG. 4.

Figure 5:
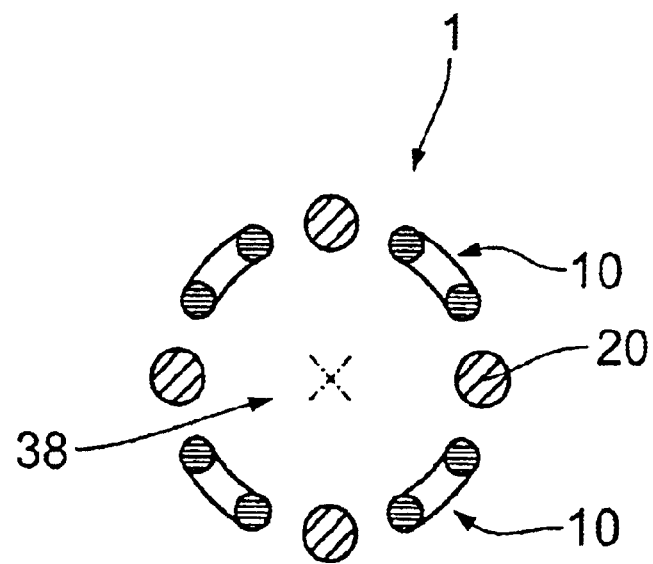
FIG. 5 is a diagrammatic view in cross-section through the stent shown in FIG. 1 in the region of the line V—V in FIG. 1.

FIG. 5 shows a highly diagrammatic view in cross-section through the stent 1, not in the expanded or developed state, in the region of the line V—V in FIG. 1, in which each tubular portion has eight elements 10. Of those eight elements 10, each second one is connected by way of connecting bars 20 to elements of an adjacent tubular portion. Overall therefore, as indicated by the larger spots 20, four elements 10 are connected by way of connecting bars 20 to elements of the adjacent portion, thus affording a four-figure axis of symmetry 38 of the tubular portions.

Figure 6:
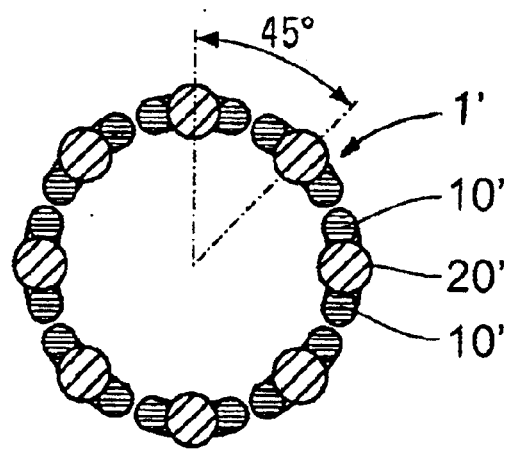
FIG. 6 is a diagrammatic view in cross-section through a stent according to the invention in which adjacent portions are turned through 45° relative to each other.

FIG. 6 shows an also highly diagrammatic projection of two adjacent tubular portions of a further stent 1' according to the invention. In this case the tubular portions 8 correspond to the portions shown in FIG. 5. However they are turned relative to each other through 45° or half a period of the peripherally extending edge contours of the portions. In this case also the larger spots 20' symbolically represent the elements 10' connected to connecting bars 20'.

As already mentioned, FIGS. 5 and 6 are highly diagrammatic views. The illustrated contours are only indicative place-markers for the sectioned parts of the stent in question and do not reproduce the actual section contour thereof.

Figure 7:
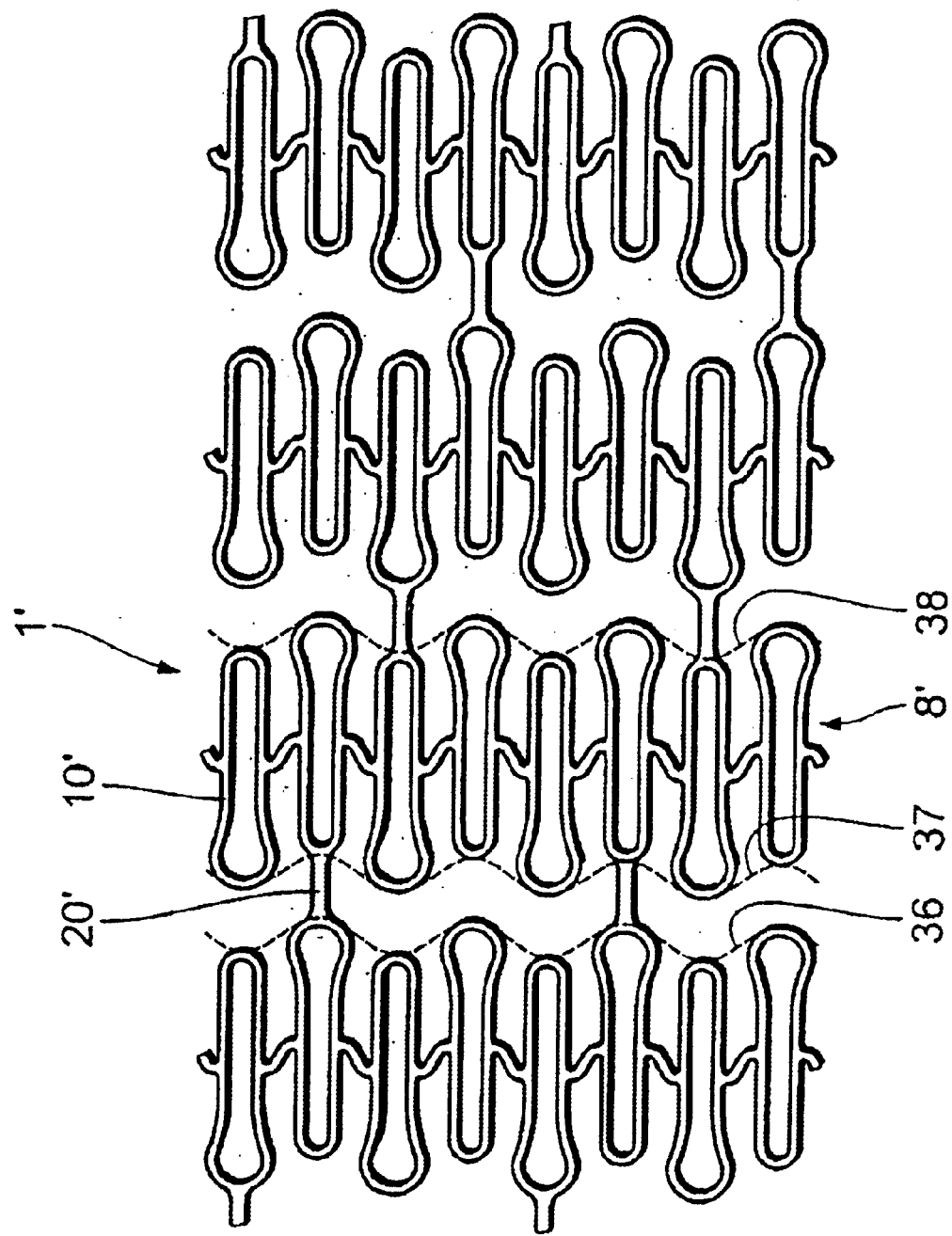
FIG. 7 shows a development of a part of the peripheral surface of a further variant of the stent according to the invention.

FIG. 7 shows a further preferred embodiment of the stent 1' according to the invention with eight elements 10' per tubular portion 8'. This embodiment is the same in terms of its fundamental structure as that shown in FIG. 1 so that only the differences will be discussed in detail here.

The difference is that there are only two respective connecting bars 20' between each two adjacent tubular portions 8' of the stent 1', wherein at each fourth element 10' a connecting bar engages the tubular portion 8' which adjoins it in a first direction. The connecting bars 20' are further displaced from one portion 8' to another portion 8' by half a period of the wave-like edge contour of the portions 8', as is indicated by the broken-line contours 36 through 38. That displaced arrangement of the connecting bars 20' affords a stent which is flexible over its length in all directions in space.

As is already the case with the embodiment shown in FIG. 1, the elements 10' of each tubular portion 8' in this variant are also so arranged in mutually displaced relationship in the longitudinal direction of the stent 1' that their ends define the described edge contours 37 and 38 which extend around the stent in a wave-like configuration with respect to the peripheral direction of the stent in in-phase relationship. Furthermore, in this case also the tubular portions 8' are so arranged relative to each other that mutually adjacent edge contours 36 and 37 of adjacent portions 8' extend in phase with each other, whereby in accordance with the invention particularly good and uniform coverage of the inside wall of the vessel is achieved in the expanded condition.

Figure 8:
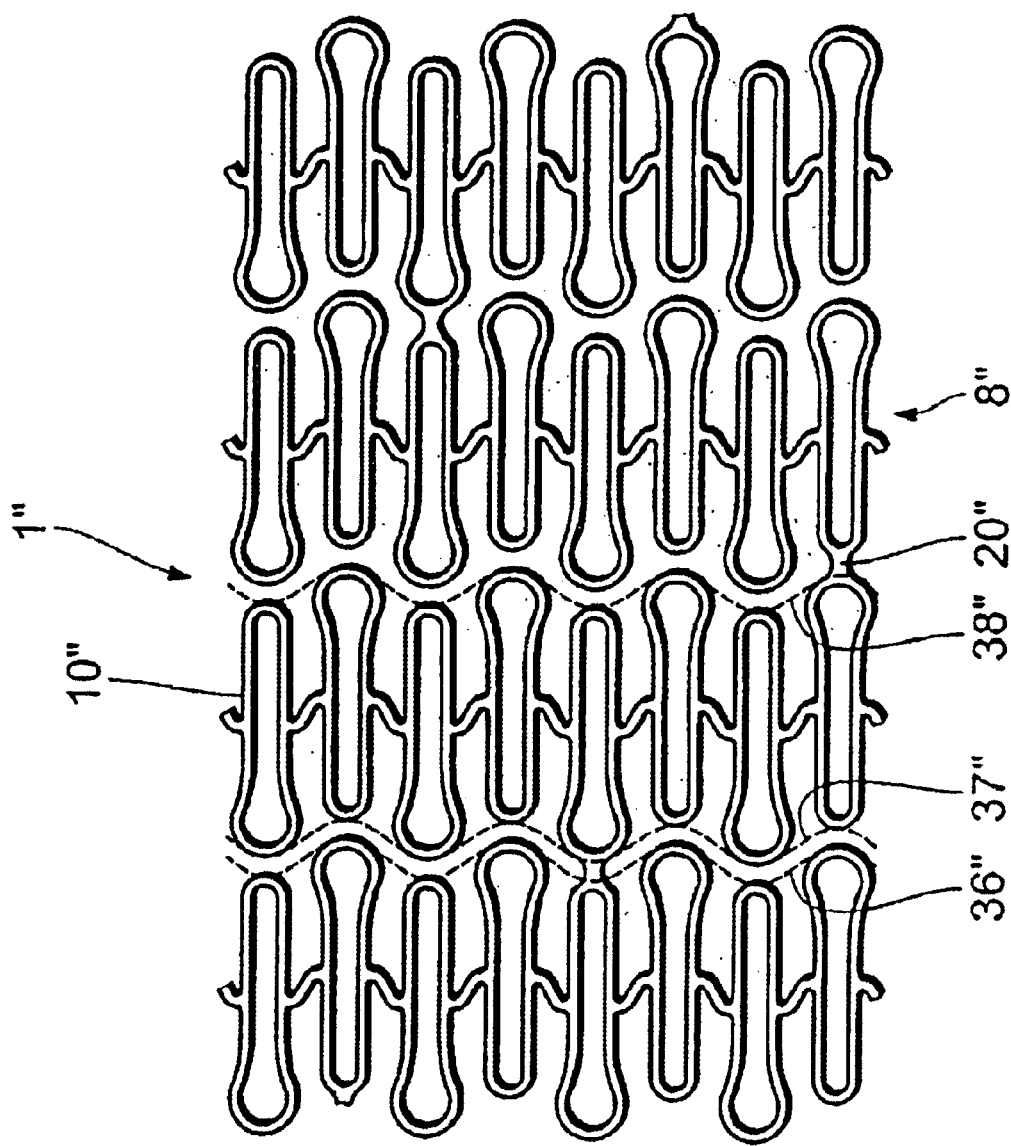
FIG. 8 shows a development of a part of the peripheral surface of another variant of the stent according to the invention.

FIG. 8 shows a further preferred embodiment of the stent 1" according to the invention, with eight elements 10" per tubular portion 8". This embodiment is the same in terms of its fundamental structure to that shown in FIG. 1 so that only the differences will be discussed here.

One difference is that there is only one respective connecting bar 20" between each two adjacent tubular portions 8" of the stent 1". The connecting bars 20" are further displaced from one portion 8" to another portion 8" by one and a half periods of the wave-like edge contour of the portions 8", as is indicated by the broken-line contours 36" through 38". The small number and the displaced arrangement of the connecting bars 20" affords a stent which is extremely flexible over its length in all directions in space.

A further difference is that the spacing in the longitudinal direction between the tubular portions 8" is selected to be so small that the edge contours 36" and 37" of adjacent tubular portions 8" engage into each other in the manner of a tooth configuration. In this case, in other words, the individual elements 10" of the one tubular portion 8" come so close to the elements 10" of the adjacent tubular portion 8" that the adjacent elements 10" partially overlap in the longitudinal direction of the stent 1". This configuration affords particularly small uniform gaps in the expanded stent structure and thus provides for extremely good coverage of the inside wall of the vessel.

Figure 9:
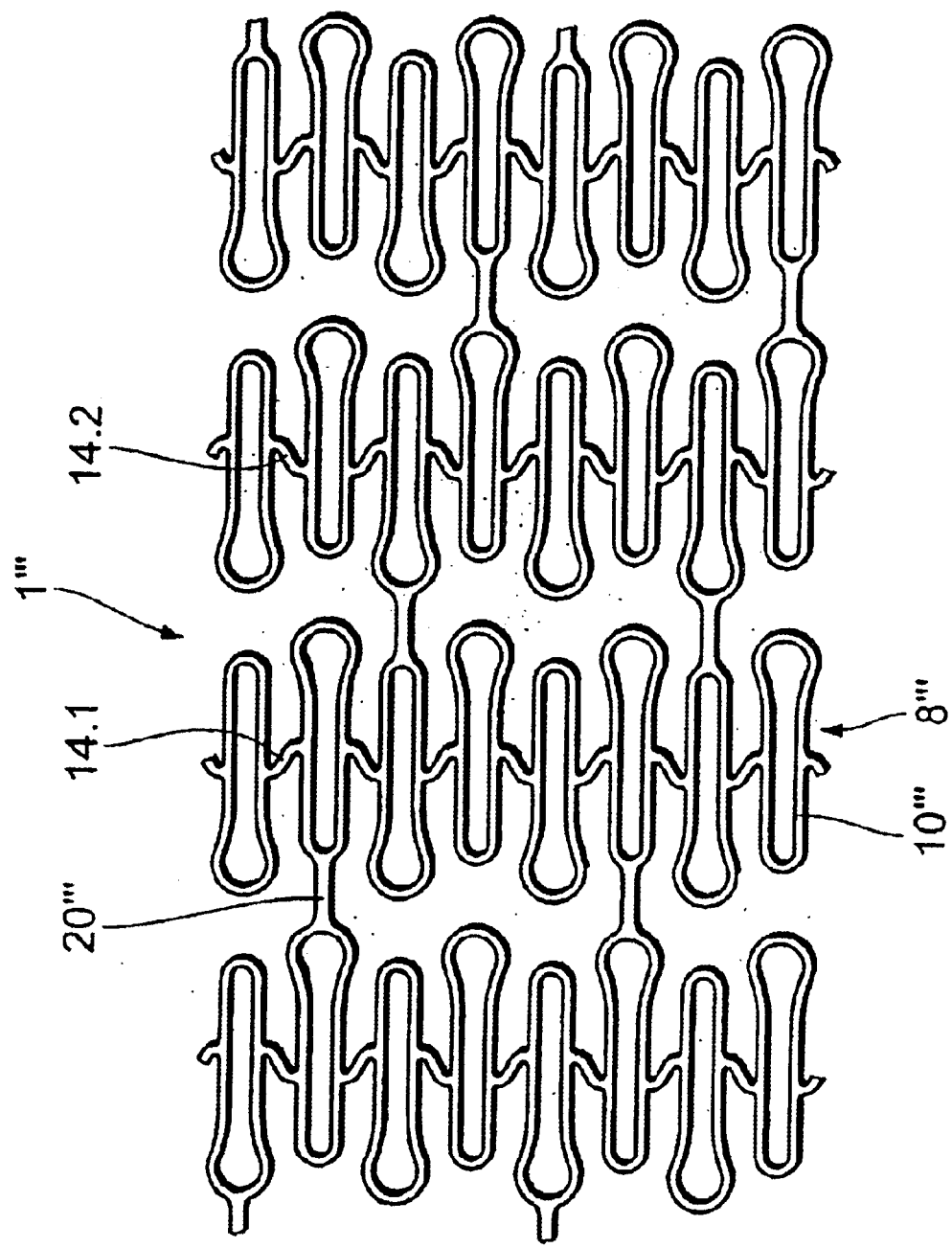
FIG. 9 shows a development of a part of the peripheral surface of a further variant of the stent according to the invention.

FIG. 9 shows another preferred variant of the stent 1''' according to the invention, which differs from the variant shown in FIG. 7 only in that second connecting bars 14.1 and 14.2, which face in the same peripheral direction, of elements 10''' which are mutually adjoining in the longitudinal direction of the stent 1''' are arranged inclinedly in opposite relationship with respect to the peripheral direction. Together with the arrangement of the first connecting bars 20''', which has already been described with reference to FIG. 1 and which is displaced by half a period of the edge contours, the FIG. 9 configuration provides for good compensation in respect of the reduction in length of the stent upon expansion thereof.

That results from the longitudinal displacement of the individual elements 10''', which occurs upon expansion and which in turn results from the orientation of the second connecting bars 14''' in the peripheral direction of the stent 1'''. That longitudinal displacement is added up by virtue of the illustrated configuration over the entire stent, whereby the reduction in length of the stent, which is caused by the reduction in length of the individual elements 10''' upon expansion of the stent, can be reduced to a minimum and possibly even to zero.

Figure 10:
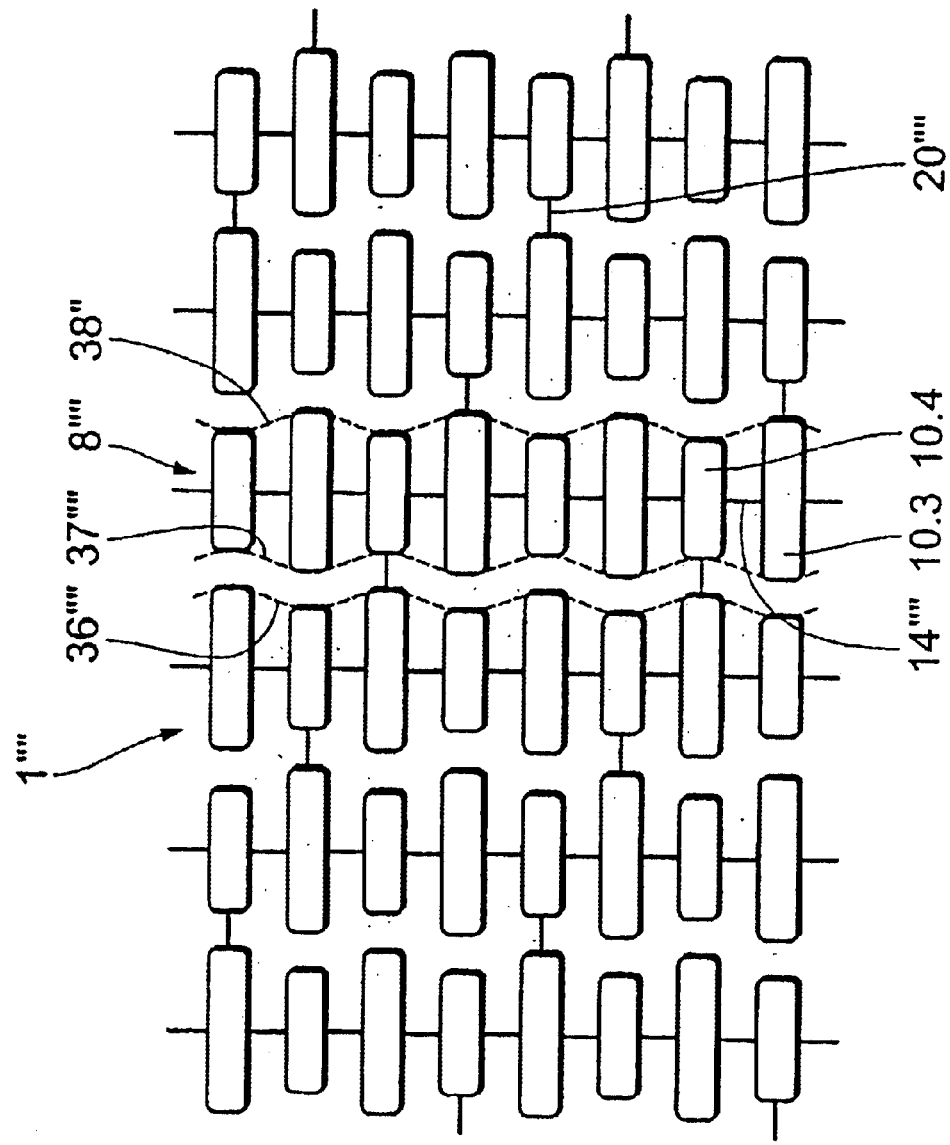
FIG. 10 is a diagrammatic development of a part of the peripheral surface of a further variant of the stent according to the invention.

FIG. 10 shows a highly diagrammatic development of the peripheral surface of a further preferred embodiment of the stent 1'''' according to the invention, with elements 10'''' forming the tubular portions 8'''', this arrangement having two different types of elements 10.3 and 10.4. In this case the elements 10.3 and 10.4 are not shown in their actual configuration but are only represented by cells of different sizes. In this case, the elements 10.3 and 10.4 can differ both in respect of their configuration and also only in respect of their dimensions.

The essential difference in this variant in relation to the above-described embodiments of the invention is the fact that, in this embodiment, by virtue of the different dimensions of the elements 10.3 and 10.4 in the longitudinal direction of the stent 1'''', the tubular portions 8'''' have edge contours 37'''' and 38'''' which extend around the stent in a wave-like configuration and which are displaced relative to each other by half a period. The center points of the elements 10.3 and 10.4, being given with respect to the longitudinal direction of the stent 1'''', are arranged in mutual alignment in the peripheral direction of the stent so that the edge contours 37'''' and 38'''' extend therearound with the same amplitude.

Otherwise, this structure also again embodies the configuration according to the invention in which the adjacent edge contours 36'''' and 37'''' of two tubular portions 8'''' extend around the stent in in-phase relationship with each other. Likewise, in this case also once again the structure involves the first connecting bars 20'''' being arranged in displaced relationship by half a period of the edge contours. The second connecting bars 14'''' are only diagrammatically shown in FIG. 10. It will be appreciated that they can be of the same arrangement and/or configuration as described above in relation to the foregoing examples. In particular, in this case also a suitable compensation for the reduction in length of the stent can again be achieved in a similar manner to the configuration already described above.

To sum up, it can be noted that this design configuration also makes it possible to achieve the same advantages as the above-described variants.

FIGS. 11a through 11d show various forms of elements 10, as can be used in mutually adjacent relationship in the tubular portions in the stents according to the invention as shown in foregoing FIGS. 1 and 7 through 10—in particular in the stent shown in FIG. 10—in place of the elements 10 through 10'''' illustrated there.

Figure 11A:
FIGS. 11a through 11d show various forms of elements for the tubular portions of a stent according to the invention.
Figure 11B:
Figure 11C:
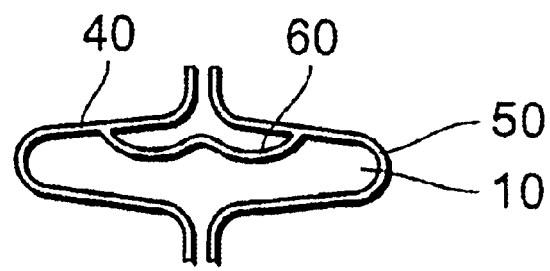
Figure 11D:
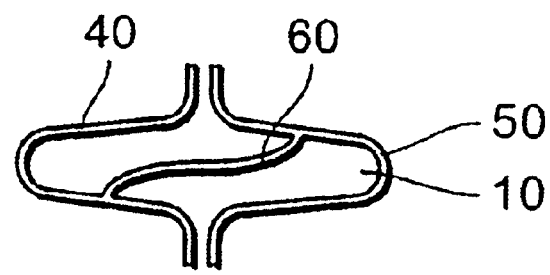

The embodiments of FIGS. 11a and 11b involve a completely closed structure while the embodiments of FIGS. 11c and 11d have two outer bars 40 and 50 which in themselves do not afford a closed structure but which by virtue of a connecting bar 60 also form closed element areas or a closed cell-shaped unit.

The stents according to the invention have been described hereinbefore by means of examples with edge contours which extend in an approximately sinusoidal configuration. It will be appreciated however that in other variants of the invention it is also possible to use other configurations with edge contours which extend around the stent in a less uniformly wave-like configuration. In particular the arrangement of the elements forming the tubular portions does not necessarily have to be respectively alternate. The elements can for example also be arranged in groups which are disposed alternately in mutually displaced relationship in accordance with the examples shown in FIGS. 1 and 7 through 9 and which in addition or alternatively may involve different dimensions in the longitudinal direction of the stent in accordance with the example shown in FIG. 10. In that respect the groups may also contain a different number of elements and additionally or alternatively also include different kinds of elements.

What is claimed is:

1. A stent, comprising:
at least two tubular portions, arranged adjacently in a longitudinal direction of the stent, each said tubular portion comprising a plurality of interconnected, substantially cell-shaped elements, the cell-shaped elements in adjacent tubular portions being aligned such that each cell-shaped element of a first tubular portion has a common central axis with a cell shaped element of a second tubular portion in a longitudinal direction of the stent, the adjacent tubular portions being connected together in the longitudinal direction of the stent by way of at least one first connecting bar that extends substantially parallel to the longitudinal direction, wherein the at least one first connecting bar directly connects cell-shaped elements of adjacent tubular portions, wherein the elements are of such a configuration that the ends of the elements which are in the longitudinal direction of the stent define an edge contour extending around the stent in a periodic wave-like configuration in a peripheral direction thereof, and wherein the mutually adjoining edge contours of adjacent tubular portions extend around the stent substantially in an in-phase relationship, and wherein the elements of at least one tubular portion are connected in the peripheral direction of the stent by way of second connected bars.

2. The stent as set forth in claim 1 wherein the edge contours of the two tubular portions engage into each other in the manner of a tooth configuration.

3. The stent as set forth in claim 2 wherein the two edge contours of one of the tubular portions extend substantially in in-phase relationship with each other or displaced substantially through half a period relative to each other.

4. The stent of claim 3 wherein the first connecting bar connects together elements of the same orientation.

5. The stent of claim 3 wherein there are no more than two first connecting bars for connecting adjacent tubular portions.

6. The stent of claim 5 wherein there are more than two tubular portions and the first connecting bars are arranged in displaced relationship over the length of the stent from one portion to another portion in the peripheral direction of the stent.

7. The stent of claim 6 wherein the first connecting bars are displaced by at least half a period of the edge contour.

8. The stent of claim 2 wherein the first connecting bar connects together elements of the same orientation.

9. The stent of claim 2 wherein the first connecting bar extends parallel to the longitudinal axis of the stent.

10. The stent of claim 9 wherein there are no more than two first connecting bars for connecting adjacent tubular portions.

11. The stent of claim 2 wherein there are no more than two first connecting bars for connecting adjacent tubular portions.

12. The stent as set forth in claim 1 wherein the two edge contours of one of the tubular portions extend substantially in in-phase relationship with each other or displaced substantially through half a period relative to each other.

13. The stent of claim 12 wherein the first connecting bar connects together elements of the same orientation.

14. The stent of claim 12 wherein the first connecting bar extends parallel to the longitudinal axis of the stent.

15. The stent of claim 14 wherein there are no more than two first connecting bars for connecting adjacent tubular portions.

16. The stent of claim 12 wherein there are no more than two first connecting bars for connecting adjacent tubular portions.

17. The stent of claim 1 wherein the first connecting bar connects together elements of the same orientation.

18. The stent of claim 17 wherein the first connecting bar extends parallel to the longitudinal axis of the stent.

19. The stent of claim 18 wherein there are no more than two first connecting bars for connecting adjacent tubular portions.

20. The stent of claim 19 wherein there are more than two tubular portions and the first connecting bars are arranged in displaced relationship over the length of the stent from one portion to another portion in the peripheral direction of the stent.

21. The stent of claim 20 wherein the first connecting bars are displaced by at least half a period of the edge contour.

22. The stent of claim 17 wherein there are no more than two first connecting bars for connecting adjacent tubular portions.

23. The stent of claim 22 wherein there are more than two tubular portions and the first connecting bars are arranged in displaced relationship over the length of the stent from one portion to another portion in the peripheral direction of the stent.

24. The stent of claim 23 wherein the first connecting bars are displaced by at least half a period of the edge contour.

25. The stent of claim 23 wherein the elements of at least one tubular portion are connected in the peripheral direction of the stent by way of second connecting bars which are arranged inclinedly with respect to the peripheral direction.

26. The stent of claim 25 wherein the second connecting means extend in an S-shape, wherein second connecting bars facing in the same peripheral direction of elements in mutually adjoining relationship in the longitudinal direction of the stent are arranged inclinedly in opposite relationship with respect to the peripheral direction.

27. The stent of claim 1 wherein there are no more than two first connecting bars for connecting adjacent tubular portions.

28. The stent of claim 27 wherein there are more than two tubular portions and the first connecting bars are arranged in displaced relationship over the length of the stent from one portion to another portion in the peripheral direction of the stent.

29. The stent of claim 28 wherein the first connecting bars are displaced by at least half a period of the edge contour.

30. The stent of claim 1 wherein there are more than two tubular portions and the first connecting bars are arranged in displaced relationship over the length of the stent from one portion to another portion in the peripheral direction of the stent.

31. The stent of claim 30 wherein there are no more than two first connecting bars for connecting adjacent tubular portions.

32. The stent of claim 30 wherein the first connecting bars are displaced by at least half a period of the edge contour.

33. The stent of claim 30 wherein the elements of at least one tubular portion are connected in the peripheral direction of the stent by way of second connecting bars which are arranged inclinedly with respect to the peripheral direction.

34. The stent of claim 1 wherein the second connecting bars are arranged inclinedly with respect to the peripheral direction.

35. The stent of claim 34 wherein there are no more than two first connecting bars for connecting adjacent tubular portions.

36. The stent of claim 35 wherein there are more than two tubular portions and the first connecting bars are arranged in displaced relationship over the length of the stent from one portion to another portion in the peripheral direction of the stent.

37. The stent of claim 36 wherein the first connecting bars are displaced by at least half a period of the edge contour.

38. The stent of claim 34 wherein the second connecting means extend in an S-shape, wherein second connecting bars facing in the same peripheral direction of elements in mutually adjoining relationship in the longitudinal direction of the stent are arranged inclinedly in opposite relationship with respect to the peripheral direction.

39. A dilation catheter comprising a stent as set forth in claim 1.

40. The stent of claim 1 wherein there are more than two tubular portions and the first connecting bars are arranged in displaced relationship over the length of the stent from one portion to another portion in the peripheral direction of the stent.

41. The stent of claim 40 wherein the first connecting bars are displaced by at least half a period of the edge contour.

* * * * *